United States Patent [19]

den Otter et al.

[11] 4,174,444

[45] Nov. 13, 1979

[54] PROCESS FOR PREPARING CYANURIC ACID

[75] Inventors: Marinus J. A. M. den Otter, Munstergeleen; Lambertus P. G. Hawinkels, Montfort; Augustinus P. H. Schouteten, Maastricht, all of Netherlands

[73] Assignee: Stamicarbon, B.V., Geleen, Netherlands

[21] Appl. No.: 890,843

[22] Filed: Mar. 27, 1978

Related U.S. Application Data

[63] Continuation of Ser. No. 703,657, Jul. 8, 1976, abandoned.

[51] Int. Cl.$^2$ ............................................. C07D 251/32
[52] U.S. Cl. ...................................................... 544/192
[58] Field of Search ......................................... 544/192

[56] References Cited

U.S. PATENT DOCUMENTS

| | | | |
|---|---|---|---|
| 3,758,572 | 9/1973 | Jones et al. | 544/192 |
| 3,954,751 | 5/1976 | Fuchs et al. | 544/192 |

Primary Examiner—Dolph H. Torrence
Attorney, Agent, or Firm—Cushman, Darby & Cushman

[57] ABSTRACT

An improved process for the manufacture of cyanuric acid by heating a reaction solution of urea, biuret, or mixtures thereof, in a solvent and stripping the reaction solution with a stripping gas. The process recycles waste gas produced by the reaction solution as the stripping gas.

5 Claims, 1 Drawing Figure

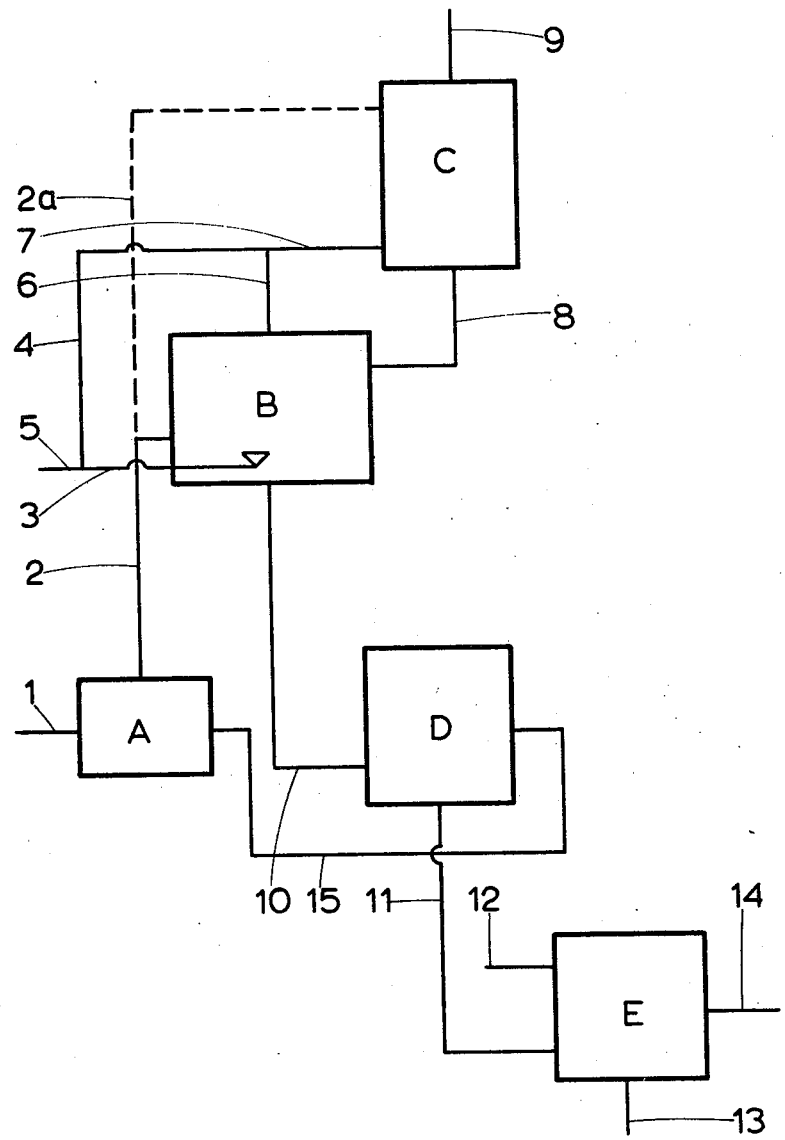

PROCESS FOR PREPARING CYANURIC ACID

This is a continuation of application Ser. No. 703,657 filed July 8, 1976, now abandoned.

BACKGROUND OF THE INVENTION

This invention relates to a process for the preparation of cyanuric acid by heating a reaction solution of urea, biuret, or mixtures thereof, dissolved in a solvent while stripping the reaction mixture with a stripping gas. Netherlands patent application No. 69.10466, and corresponding U.S. Pat. No. 3,635,968, describe such a process wherein N-cyclohexyl pyrrolidone is employed as a solvent and an inert gas such as nitrogen or carbon dioxide is passed through the reaction mixture to remove ammonia which forms during the reaction.

A problem which exists in such known processes resides in the fact that the valuable by-product ammonia must be recovered from a gaseous mixture which, of course, is highly diluted with the inert gas. Such recovery methods entail undesirably high costs. Such is also true with regard to recovery of gaseous solvent which may be contained in the vented waste gas from the reaction mixture. When the stripping treatment is omitted from such processes, one obtains an unsuitable product which is highly contaminated with aminated by-products such as ammelide and ammeline.

It is important to obtain cyanuric acid having a low content of aminated by-products, since, generally, an aminated byproduct content of over one percent is commercially unacceptable. Therefore, crude cyanuric acid having an aminated by-product content in excess of one percent by weight is generally purified by treatment with an aqueous solution of a strong acid to hydrolyze ammelide and ammeline to cyanuric acid. However, such a hydrolysis step is expensive and, thus, it would be desirable to avoid same if possible.

Accordingly, it is the primary object of the present invention to provide a process for producing cyanuric acid whereby by-product ammonia may be readily separated from waste gases resulting from the reaction mixture.

It is a further object of the present invention to provide a process for preparing cyanuric acid having a low aminated by-product content.

These and other objects of the present invention will be readily apparent from the description which follows.

DESCRIPTION OF THE INVENTION

Cyanuric acid is prepared according to the present invention by reacting a solution of urea, biuret, or mixtures thereof, in a solvent in a reaction zone at an elevated temperature while simultaneously stripping the reaction mixture with a stripping gas which is composed of waste gas resulting from the reaction mixture in the reaction zone.

According to the present invention, it is unnecessary to feed an inert gas to the reaction zone for stripping as at least part of the waste gas, which is composed of ammonia and solvent vapor, is recycled to the reactor. The remainder of the waste gas is vented. As a result, the vented gas, according to the present invention, contains a higher concentration of ammonia than in prior processes such as described in Netherlands patent application No. 69.10466 and U.S. Pat. No. 3,635,968, thus providing a more efficient and less expensive means for recovering ammonia. Moreover, the amount of solvent vapor in the vent gas is less than the total amount in the waste gas, thereby providing a considerable cost saving in solvent recovery.

According to U.S. Pat. No. 2,943,088, the presence of ammonia in the conversion of urea into cyanuric acid results in a cyanuric-acid product having a higher content of aminated by-product. Surprisingly, we have found in the present invention that stripping of the reaction mixture with ammonia or a gaseous mixture high in ammonia content does not produce a highly-aminated cyanuric acid product, but, rather, a product having less than one percent by weight of aminated by-product, thereby eliminating the necessity of a hydrolysis treatment.

A further advantage of the present invention resides in the fuel savings attendant recycling at least a part of the waste gas from the reactor, thereby recovering some of the heat content. Unlike known processes wherein the heat content of the waste gas is lost from the system in recovery of ammonia and solvent, in the present process, only a fraction of the heat is lost with the portion of waste gas vented.

Still another advantage of the present process is the ease by which the supply of gas to the reactor may be increased, simply by raising the recycling ratio of the waste gas which requires only a small amount of energy and, of course, eliminates the need to reduce the concentration of ammonia in the waste gas. As a result, the stirring or agitation action of the recycle waste gas fed into the reactor can be increased with little expense. Under these circumstances, a mechanically-unstirred round gas reactor may be used and the superficial gas velocity at which stripping gas is fed to the reactor may suitably range from about 0.1 to 1.0 and preferably 0.3 to 0.5 m/sec. The reaction mixture may be suitably stripped, for example, by bubbling the stripping gas through the mixture such that the mixture is contacted with the gas. Superficial gas velocity as used herein refers to superficial mass velocity as defined by Perry's Chemical Engineer's Handbook, Fourth Edition, pages 5-15, 1963, which is incorporated herein by reference.

The solvent used in the present process must be such that urea, biuret, and mixtures thereof, are soluble therein, by cyanuric acid is substantially insoluble. Furthermore, the solvent must be inert to the reactants and stable at the temperatures employed, thus having a high boiling point.

A wide variety of solvents are suitable for the process, including, for example, dialkyl sulfones or cyclic sulfones having up to 12 carbon atoms, halogen-substituted cresols and phenols, N-alkyl pyrrolidones, N-substituted urethanes and cyclic urethanes having phenyl or alkyl groups with up to six carbons as substituents, and cyclohexanol, which, if desired, may be substituted with at least one hydrocarbon group having up to six carbon atoms. Suitable hydrocarbon groups include phenyl, alkyl or cycloalkyl groups. Thus, suitable solvents include dimethyl sulfone, dipropyl sulfone, sulfolane, chlorocresols, 5-methyl-2-oxazolidinene, 2-methyl cyclohexanol, 2,6-dimethyl cyclohexanol, and 2,4,6-trimethyl cyclohexanol. Preferred solvents include sulfolane and derivatives thereof having one or more methyl groups.

A catalyst which is soluble in the reaction mixture is preferably employed. The catalyst may be an acid, acid anhydride, or ammonium salt of an acid. The catalyst is preferably organic and should not be very volatile under reaction conditions and thus should have a higher boiling point at reaction pressure than the temperature at which the reaction is carried out. Furthermore, the catalyst must have sufficient thermal stability under reaction conditions so as not to decompose. Suitable catalysts include such organic acids as both saturated id unsaturated high-boiling aliphatic carboxylic acids containing up to 24 carbon atoms, aromatic carboxylic acids having up to 12 carbon atoms, both aliphatic and aromatic dicarboxylic acids having up to 12 carbon atoms and similar polycarboxylic acids, as well as the anhydrides and ammonium salts of the afore-mentioned acids.

As examples of suitable catalysts, to note but a few, include palmitic acid, oleic acid, stearic acid, benzoic acid, toluene carboxylic acids, naphthoic acids, phenyl acetic acid, succinic acid, phthalic acid, and 1,3,5-pentane tricarboxylic acid, as well as the anhydrides and ammonium salts of these acids. The acid, anhydride or ammonium salts may, if desired, contain substituents which are inert under reaction conditions such as alkyl groups from one to four carbon atoms, aryl groups having up to eight carbon atoms, or halogen substituents. Preferred catalysts which are readily available include benzoic acid and ammonium benzoate.

The amount of catalyst which is added to the reaction mixture may vary greatly, but is noticeably effective at concentrations as low as 0.1% by weight of the total reaction mixture. While addition of more than 150 g/liter of catalyst is permissible, such does not generally provide any advantage and, thus, the amount of catalyst added generally ranges from about 10 to about 150 grams per liter of the reaction mixture.

The reaction temperature may vary widely, and generally ranges from about 150 to about 280° C. Preferably, the reaction is carried out at from about 170° to about 220° C. with an optimum being about 200° C. when sulfolane, or a derivative thereof, is the solvent. While the reaction may proceed more rapidly at higher temperatures, there is a greater change of forming additional ammelide by-product and decomposing the solvent.

The reaction pressure is not critical and may also vary widely, ranging, for example, from about 0.01 to 10 atmospheres. Suitably, the reaction may be carried out at about atmospheric pressure, for example, between about 0.5 and 2 atmospheres. In some instances, it may be advantageous to carry the reaction out at below atmospheric pressure, suitably in the range of from about 0.01 to 0.25 atmospheres.

In order to avoid undesirably-high concentrations of ammelide in the cyanuric acid product, the concentration of the urea and/or biuret starting material should be kept low, preferably at a level of 600 grams/liter of reaction mixture or less. However, higher concentrations may be used but amounts in excess of the saturation level offer no advantage. Preferably, the concentration of urea, biuret, or mixtures thereof, ranges from about 200 to about 400 grams/liter.

As noted above, at least a portion of the waste gas exiting the reactor is recycled, and this may range suitably from about 60 to 99.9 percent by volume of the waste gas. The recycle waste gas is fed to the reactor so as to provide a degree of agitation in the reaction mixture which enhances the reaction. The stripping waste gas, together with any additional stripping gas which may be used, is added to the reactor suitably at a rate of from 50 to 1.000 liter per hour per liter of reaction mixture.

The process according to the present invention may be carried out suitably, either batchwise or as a continuous process.

With reference to the accompanying drawing which schematically depicts the process according to the present invention, urea, biuret, or mixtures thereof, are fed to a tank A through line 1 for dissolving in the solvent. The resulting solution flows through line 2 to reaction vessel B which may be preferably be a gas scrubber wherein the conversion reaction to cyanuric acid is carried out. Waste gas which develops in B escapes through line 6 and a portion is recycled through a line 4 and fed as a stripping gas to B by way of line 3. If desired, additional stripping gas such as ammonia, nitrogen, or carbonic acid, may be introduced to the reactor via line 5. Indeed, such additional stripping gas may be necessary when the process is initially started due to the low amount of ammonia which is recycling through lines 6, 4 and 3. The gaseous mixture which escapes from the reactor B at 6 is composed generally of solvent vapor, ammonia and additional stripping gas, if added. The portion of waste gas which is not recycled to B through lines 3 and 4 is fed, via line 7, to condenser C which may be a scrubber wherein the wash liquid is preferably a solution of the starting material supplied by line 2a. Gas which is not condensed in C is vented through line 9, and, generally, contains relatively pure ammonia or a mixture of stripping gas rich in ammonia which can easily be recovered. Condensed solvent which forms in C flows back to the reactor B through line 8.

A suspension of cyanuric acid in the solvent flows from reactor B through line 10 to separator D. Here the cyanuric acid is separated off by filtration, precipitation, decantation, or in another suitable manner. The solid product is passed through line 11 to washing installation E, where it is washed with washing liquid supplied through line 12. The washing liquid used may be, for example, water, which leaves the washing installation through line 13. Pure cyanuric acid is discharged through line 14. If desired, the cyanuric-acid product leaving D through 11 may be subjected in a conventional manner to acid hydrolysis with a strong mineral acid, such as nitric acid, in order to hydrolyze the by-products ammelide and ammeline to cyanuric acid. Normally, however, this is not necessary, as the ammelide content of the cyanuric acid is already sufficiently low for most applications. The mother liquor departed off in D, which often still contains unconverted urea, biuret, or a mixture of the two, and is saturated with cyanuric acid, is fed back to dissolving vessel A through line 15.

In a continuous operation, according to the present invention, at the outset, a given amount of solvent and catalyst, if present, are placed in reactor B. Solvent and catalyst are recycled throughout the process with any losses being replenished through conduits (not shown) located somewhere in the system, preferably the reactor. Stripping gas, which is preferably ammonia, is initially added at 5 in a continuous operation. The reaction commences upon heating the contents of the reactor after which ammonia is formed from the reaction mixture and, consequently, the initial feed of ammonia or other additional stripping gas through 5 may be reduced or discontinued.

The following examples and comparative experiments are provided to more fully illustrate the invention, but are not to be construed as limiting the scope thereof.

benzene and dried. The results are set forth in columns 8 and 9.

| 1 | 2 | 3 | 4 | 5 | 6 | 7 | 8 | 9 |
|---|---|---|---|---|---|---|---|---|
| Example | Amount Of Urea (Grams) | Catalyst (Grams) | Stripping Gas Rate (1/h) | Stripping Gas | Reaction Temperature °C. | Reaction Time (Hours) | Cyanuric Acid Production (Grams/Hr.) | Amount Of Ammelide* |
| I | 250 | 150A | 600 | $NH_3$/waste/gas | 190 | 2 | 13 | 0.8 |
| Comparative Experiment A | 250 | 150A | — | None | 190 | 1 | 8 | 0.8 |
| II | 280 | 75B | 300 | $NH_3$/waste gas | 200 | 1 | 13 | 2.0 |
| Comparative Experiment B | 280 | 75B | 300 | $CO_2$ | 200 | 1 | 16 | 3.0 |

*The ammelide content is the combined total amount of ammelide and ammeline.
A denotes ammonium benzoate.
B denotes benzoic acid.

EXAMPLES AND COMPARATIVE EXPERIMENTS

Referring to the table below, in each of Examples I and II, as well as Comparative Experiments A and B, 1 kg of sulfolane is heated with stirring to 160° C. in a reactor. To the heated sulfolane, urea, in the amount indicated in column 1, is fed to the reactor to form a reaction solution which is heated to the reaction temperature noted in column 6. Upon reaching the reaction temperature indicated, 99% of the waste gas from the reactor is recycled as a stripping gas to the reaction solution after having been made up with ammonia to the amount indicated in column 4. With the formation of ammonia as a reaction product, the amount of added ammonia to the stripping gas is lowered so as to maintain a constant total amount of stripping gas. When the amount of ammonia added is reduced to zero, the amount of stripping gas added to the reactor is maintained constant at the value indicated by controlling the amount of waste gas which is recycled. In each case, the reactor pressure is maintained at one atmosphere.

None of the waste gas from the reaction is recycled to the Comparative Experiments. In Comparative Experiment A, no stripping gas is employed, whereas in Experiment B, $CO_2$ is added.

The reaction time set forth in column 7 is measured from the time at which the reaction temperature is reached and stripping begun.

After the reaction is completed, stripping is discontinued and the resulting reaction mixture is cooled to 30° C. and filtered. The resulting filter cake is washed with The solid substance filtered off contains unconverted urea and biuret which have crystallized. If the reaction mixture is filtered at higher temperatures, only traces of other impurities than ammelide and ammeline are contained in the cyanuric-acid product.

The invention, in its broadest aspects, is not limited to the specific details shown and described, but departures may be made from such details within the scope of the accompanying claims, without departing from the principles of the invention. Furthermore, the invention claimed herein may comprise, consist of, or consist essentially of the hereinabove-recited steps and materials.

We claim:

1. In a process for the preparation of cyanuric acid by heating a reaction solution of urea, biuret, or mixtures thereof, in a solvent and stripping the solution with a stripping gas to remove ammonia therefrom, the improvement which comprises employing waste gas resulting from heating said reaction solution as the stripping gas by recycling at least 60% by volume of said waste gas to the reaction solution.

2. A process according to claim 1 wherein a second stripping gas is used in addition to the waste gas.

3. A process according to claim 2 wherein said second stripping gas is ammonia.

4. A process according to claim 1 wherein the stripping gas is fed to the reaction solution at a superficial gas velocity from about 0.1 to about 1.0 m/sec.

5. A process according to claim 4 wherein the superficial gas velocity is from about 0.3 to 0.5 m/sec.

* * * * *